(12) United States Patent
Dake et al.

(10) Patent No.: US 11,413,289 B2
(45) Date of Patent: *Aug. 16, 2022

(54) INHALABLE IMATINIB FORMULATIONS, MANUFACTURE, AND USES THEREOF

(71) Applicant: Aerovate Therapeutics, Inc., Boston, MA (US)

(72) Inventors: Ben Dake, Boston, MA (US); Ralph Niven, Portola Valley, CA (US)

(73) Assignee: Aerovate Therapeutics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/874,122

(22) Filed: May 14, 2020

(65) Prior Publication Data

US 2020/0360377 A1 Nov. 19, 2020

Related U.S. Application Data

(60) Provisional application No. 62/984,037, filed on Mar. 2, 2020, provisional application No. 62/958,481, filed on Jan. 8, 2020, provisional application No. 62/942,408, filed on Dec. 2, 2019, provisional application No. 62/877,575, filed on Jul. 23, 2019,
(Continued)

(51) Int. Cl.
| | | |
|---|---|---|
| *A61K 31/506* | (2006.01) | |
| *A61K 9/00* | (2006.01) | |
| *A61P 11/00* | (2006.01) | |
| *A61K 38/18* | (2006.01) | |
| *A61K 38/19* | (2006.01) | |
| *A61P 9/12* | (2006.01) | |

(Continued)

(52) U.S. Cl.
CPC .......... *A61K 31/506* (2013.01); *A61K 9/0073* (2013.01); *A61K 9/0075* (2013.01); *A61K 9/0078* (2013.01); *A61K 31/501* (2013.01); *A61K 38/1858* (2013.01); *A61K 38/193* (2013.01); *A61K 47/26* (2013.01); *A61P 9/12* (2018.01); *A61P 11/00* (2018.01); *C07B 2200/13* (2013.01)

(58) Field of Classification Search
CPC .. A61K 31/506; A61K 31/501; A61K 9/0073; A61K 9/0075; A61K 9/0078; A61K 47/26; C07B 2200/13
See application file for complete search history.

(56) References Cited

U.S. PATENT DOCUMENTS

| | | |
|---|---|---|
| 5,521,184 A | 5/1996 | Zimmermann |
| 7,507,821 B2 | 3/2009 | Anli et al. |

(Continued)

FOREIGN PATENT DOCUMENTS

| | | | | |
|---|---|---|---|---|
| CN | 103910711 A | * | 7/2014 | .......... C07D 401/04 |
| EP | 2582689 A1 | | 4/2013 | |

(Continued)

OTHER PUBLICATIONS

Freyhaus, 2009, Significant improvement of right ventricular function by imatinib mesylate in scleroderma-associated pulmonary arterial hypertension, Clin Res Cardiol 98:265-267.
(Continued)

*Primary Examiner* — Lakshmi S Channavajjala
(74) *Attorney, Agent, or Firm* — Brown Rudnick LLP

(57) ABSTRACT

The invention relates to inhalable imatinib formulations, manufacture, and uses thereof.

8 Claims, 13 Drawing Sheets

Related U.S. Application Data provisional application No. 62/849,056, filed on May 16, 2019, provisional application No. 62/849,059, filed on May 16, 2019, provisional application No. 62/849,058, filed on May 16, 2019, provisional application No. 62/849,054, filed on May 16, 2019.

(51) Int. Cl.
  *A61K 47/26* (2006.01)
  *A61K 31/501* (2006.01)

(56) References Cited

U.S. PATENT DOCUMENTS

| | | | |
|---|---|---|---|
| 7,638,627 | B2 | 12/2009 | Kankan et al. |
| 7,674,901 | B2 | 3/2010 | Szczepek et al. |
| 9,925,184 | B2 | 3/2018 | Zisman |
| 2006/0094674 | A1* | 5/2006 | Neel ................ A61K 45/06 514/44 A |
| 2006/0223817 | A1 | 10/2006 | Adin et al. |
| 2006/0275372 | A1 | 12/2006 | Jenkins et al. |
| 2008/0103305 | A1 | 5/2008 | MacDonald et al. |
| 2008/0181958 | A1 | 7/2008 | Rothrock et al. |
| 2008/0207904 | A1 | 8/2008 | MacDonald et al. |
| 2009/0136579 | A1 | 5/2009 | Egashira |
| 2010/0330130 | A1 | 12/2010 | Khunt et al. |
| 2011/0190313 | A1 | 8/2011 | Pascoe et al. |
| 2011/0275097 | A9 | 11/2011 | Singh et al. |
| 2011/0281867 | A1 | 11/2011 | Kalman et al. |
| 2011/0306763 | A1 | 12/2011 | Kamath et al. |
| 2012/0192861 | A1 | 8/2012 | Surber |
| 2013/0060030 | A1 | 3/2013 | Kompella et al. |
| 2013/0310424 | A1 | 11/2013 | Surber |
| 2015/0044288 | A1* | 2/2015 | Surber ................ A61K 47/12 424/489 |
| 2015/0196543 | A1 | 7/2015 | Surber |
| 2017/0224706 | A1 | 8/2017 | Surber |
| 2018/0162837 | A1 | 6/2018 | Zisman |
| 2018/0263995 | A1 | 9/2018 | Schmidt et al. |
| 2018/0325917 | A1 | 11/2018 | Surber |
| 2019/0030012 | A1 | 1/2019 | Surber |
| 2019/0054076 | A1 | 2/2019 | Surber |
| 2020/0060968 | A1 | 2/2020 | Surber et al. |
| 2020/0306264 | A1 | 10/2020 | Surber |
| 2020/0405704 | A1 | 12/2020 | Surber |

FOREIGN PATENT DOCUMENTS

| | | |
|---|---|---|
| WO | 2006/133046 A2 | 12/2006 |
| WO | 2007/119601 A2 | 10/2007 |
| WO | 2008/136010 A1 | 11/2008 |
| WO | 2010/019540 A1 | 2/2010 |
| WO | 2011/023146 A1 | 3/2011 |
| WO | 2011/039782 A1 | 4/2011 |
| WO | 2011/095835 A1 | 8/2011 |
| WO | 2011/100282 A2 | 8/2011 |
| WO | 2012/090221 A1 | 7/2012 |
| WO | 2019/060463 A2 | 3/2019 |

OTHER PUBLICATIONS

Ghofrani, 2005, Imatinib for the Treatment of Pulmonary Arterial Hypertension, N Engl J Med, 353(13):1412-1413.

Ghofrani, 2010, Imantinib in Pulmonary Arterial Hypertension Patients with Inadequate Response to Established Therapy, American Journal of Respiratory and Critical Care Medicine, 182:1172-1177.

Hoeper, 2013, Imatinib Mesylate as Add-on Therapy for Pulmonary Arterial Hypertension, Results of the Randomized IMPRES Study, 122 pages.

Novartis Study Shows QT1571 Significantly Improved Walking Distance in Patients with Life-Threatening Pulmonary Arterial Hypertension, 2011, 5 pages.

Schermuly, 2005, Reversal of experimental pulmonary hypertension by PDGF inhibition, J Clin Invest, 115(10):2811-2821.

International Search Report and Written Opinion issued in International Application No. PCT/US2020/032872, dated Sep. 28, 2020, 16 pages.

International Search Report and Written Opinion issued in International Application No. PCT/US2020/032874, dated Jul. 21, 2020, 7 pages.

Kesely, 2016, Inhibition of an Erythrocyte Tyrosine Kinase with Imatinib Prevents Plasmodium falciparum Egress and Terminates Parasitemia, PLoS One, vol. 11, No. 10.

* cited by examiner

303 — micronizing imatinib particles

305 — suspending the micronized imatinib particles in a solution

307 — spray drying the suspended micronized imatinib particles

INHALABLE IMATINIB FORMULATIONS, MANUFACTURE, AND USES THEREOF

CROSS-REFERENCE TO RELATED APPLICATIONS

This Application claims the benefit of, and priority to, U.S. Provisional Application Nos. 62/849,054, filed May 16, 2019; 62/849,056, filed May 16, 2019; 62/849,058, filed May 16, 2019; 62/849,059, filed May 16, 2019; 62/877,575, filed Jul. 23, 2019; 62/942408, filed Dec. 2, 2019; 62/984, 037, filed Mar. 2, 2020; and 62/958,481, filed Jan. 8, 2020; the content of each of which is hereby incorporated by reference herein in its entirety.

FIELD OF THE INVENTION

The invention relates to inhalable imatinib formulations, manufacture, and uses thereof.

BACKGROUND

Pulmonary arterial hypertension (PAH) is a condition involving elevated blood pressure in the arteries of the lungs with unknown causes and is differentiated from systemic hypertension. PAH is a progressive disease where resistance to blood flow increases in the lungs causing damage to the lungs, the pulmonary vasculature and the heart that can eventually lead to death. While symptoms are treatable with vasodilators and other medications, there is no known disease modifying therapy or cure and advanced cases can eventually require lung transplants. Imatinib, especially the mesylate salt thereof, is a tyrosine kinase inhibitor approved for use in treating certain types of cancer. Imatinib's potential to inhibit the tyrosine kinase platelet-derived growth factor receptor (PDGFR) which is highly upregulated in the pulmonary arteries in cases of PAH, led to interest in its use in treating PAH. See, Olschewski, H, 2015, Imatinib for Pulmonary Arterial Hypertension—Wonder Drug or Killer Drug? Respiration, 89:513-514, incorporated herein by reference. To that end, studies have been conducted to determine the potential of imatinib in treating PAH and patients have been found to respond favorably to said treatment. Unfortunately, an unacceptable amount of severe adverse events including subdural hematoma blunted enthusiasm for the drug. Frost, et al., 2015, Long-term safety and efficacy of imatinib in pulmonary arterial hypertension, J Heart Lung Transplant, 34(11):1366-75, incorporated herein by reference.

SUMMARY

Compositions and methods of the invention address problems with imatinib-based PAH treatments through the use of specialized formulations and delivery mechanisms. Particularly, the invention recognizes that crystalline form and polymorph composition of drugs like imatinib and salts thereof can have significant effects on drug solubility, delivery, absorption, and metabolism. Accordingly, crystal form can be important for determining dosage and predicting patient response.

In that manner, the invention provides inhalable formulations of imatinib and salts thereof that offer greater lung exposure than equivalent doses of imatinib or imatinib mesylate administered through conventional oral routes or by IV. Accordingly, a relatively high oral dose of imatinib or imatinib mesylate would be required to achieve the same target lung exposure as achieved by inhalation of the inventive formulations. Therefore, the use of inhalable formulations of the invention allows for therapeutic amounts of imatinib to reach the lungs for treatment of PAH and other conditions of the pulmonary cardiovascular system without the adverse events experienced with prolonged oral administration of imatinib mesylate.

In particular, compounds and methods of the invention provide imatinib or a salt thereof in an inhalable form having entirely or almost entirely a single crystal form (e.g., greater than 80%, 85%, 90%, 95%, 99% or 100% of a single crystal form), thereby allowing for controlled and predictable dosing and patient response. In certain embodiments, greater than 95% of imatinib or a salt thereof in the inhalable formulation may be present in a single crystal form. Various crystal forms are discussed in detail below and x-ray powder diffraction diagrams are provided.

In certain embodiments inhalable imatinib compounds may be micronized through wet or dry milling (e.g., jet milling) to achieve the desired particle size for dry powder formulations for inhalation. Imatinib or appropriate salts thereof may be micronized to particle sizes of about 0.5 µm to about 5 µm mass median aerodynamic diameter (MMAD) for desired deep lung penetration. Inhaled products can be limited in terms of mass of powder that can be administered and certain imatinib salts will contribute significantly to the molecular weight of the inhaled compound. Accordingly, in certain embodiments, the imatinib free base may be preferred for efficient delivery of the active moiety to lung tissue. If required, various excipients or carriers can be added to imatinib or salts thereof before or after micronization depending on application. For example, carriers, excipients, conditioners, and force control agents may be included with lactose (which may be conditioned with various solvents to increase separation of imatinib during inhalation), magnesium stearate, leucine, isoleucine, dileucine, trileucine, lecithin, distearylphosphatidylcholine (DSPC) or other lipid-based carriers, or various hydrophilic polymers. The skilled artisan will appreciate that excipients or carriers are optional and that many embodiments of the invention do not require excipients or carriers.

Another advantage of the compounds and methods of the invention is the ability to exclude all or most amorphous imatinib from the formulation, even after micronization. As noted above, because crystal form can be important to drug pharmacokinetics and dosing, as well as physicochemical stability and avoiding amorphous content can therefore be important to providing predictable and efficient therapy.

Because the inhalable formulations described herein can modulate the uptake of imatinib in the target tissue of the lungs or microvasculature, formulations of the invention can be used to treat various conditions of the pulmonary cardiovascular system while avoiding the adverse events associated with higher doses that are administered by other routes of administration that introduce the drug systemically prior to reaching the target tissue. For example, compounds and methods of the invention can be used to treat PAH as well as lung transplant rejection, pulmonary veno-occlusive disease (PVOD) and pulmonary hypertension secondary to other diseases like heart failure with preserved ejection fraction (HFpEF) or schistosomiasis. Dose ranges can include between about 10 mg to about 100 mg per dose for inhalation on a twice to four times per day schedule. About 0.1 mg to about 20 mg of the active imatinib compound may then be present within the lungs after inhalation.

In certain embodiments, formulations of the invention can include processing and administration of imatinib in free base form. Free base imatinib formulations of the invention can retain crystallinity after micronization and are less hygroscopic than certain imatinib salts. Accordingly, compounds and methods of the invention include inhalable formulations of free base imatinib.

Methods and formulations of the invention may include spray-dried imatinib or salts thereof for inhalation. While carriers such as lactose may be used after micronization to aid in delivery via inhalation, those carriers may generally comprise larger diameter particles and complication in the separation of the active imatinib compound may result in lower amounts of the inhaled compound reaching the lungs. Furthermore, the amount of active compound reaching the lungs may be less predictable using such carriers and methods, making dosing more complicated. Accordingly, spray-dried methods may be used wherein imatinib or salts thereof along with various excipients or other additives may be micronized to a desired particle size and suspended or solubilized for spray-drying and inhalation.

In certain embodiments, the micronized imatinib is suspended in a feedstock for the purposes of spray-drying to avoid the creation of amorphous or polymorphic imatinib content that may occur if dissolved in a solution (e.g. in an appropriate organic solvent or within an acidified aqueous solution) upon spray-drying. By creating a stable suspension of micronized imatinib for spray-drying, once dried, the inhalable formulation can retain the desired crystal structure, particle size, and low levels of amorphous content obtained before the micronization process.

Stable suspensions for spray-drying may be obtained through manipulation of factors affecting imatinib solubility such as pH, ionic strength, and dispersing agents or surfactants. Excipients that may be used before micronization in the spray-drying methods described above include, for example, leucine, dileucine, trileucine, bulking agents such as trehalose or mannitol, lecithin, DSPC or other lipid-based carriers, citrate, or acetate.

Aspects of the invention include an inhalable formulation comprising imatinib or a salt thereof, wherein greater than 95% of the imatinib or salt thereof in the inhalable formulation is present in a single crystal form, with the proviso that the salt is not mesylate.

The single crystal form may be type A as defined herein. In certain embodiments, the single crystal form may be type B as defined herein. Inhalable formulations of the invention may include greater than 99% of the imatinib in a single crystal form. In various embodiments, 100% of the imatinib in the inhalable formulation may be present in a single crystal form.

The inhalable formulation may be in a dry powder. In some embodiments, the inhalable formulation may be a suspension of crystalline imatinib. The imatinib may be present in a therapeutically effective amount to treat a condition of the pulmonary cardiovascular system, such as pulmonary arterial hypertension (PAH). The salt may be at least one selected from the group consisting of glycollate, isethionate, xinafoate, furoate, trifenatate, HCl, sulfate, phosphate, lactate, maleate, malate, fumarate, tartrate, succinate, adipate, citrate, and malonate. In preferred embodiments, the salt may be glycolate, malate, tartrate, malonate, isethionate, or citrate. The inhalable formulation may further include one or more carrier agents.

Certain aspects of the invention may include methods of treating a condition of the pulmonary cardiovascular system including providing to a subject an inhalable formulation comprising imatinib or a salt thereof, wherein greater than 95% of the imatinib or salt thereof in the inhalable formulation is present in a single crystal form, with the proviso that the salt is not mesylate.

In certain aspects, methods of the invention may include preparing an inhalable formulation by micronizing imatinib particles, suspending the micronized imatinib particles in a solution, and spray drying the suspended micronized imatinib particles. Under this approach, inhalable micronized particles are modified such that they can be delivered more readily from an inhaler device and show better lung deposition, while retaining the original form of the API to allow for modulation of residence time in the lungs (i.e. slowed dissolution rate relative to amorphous drug).

The micronized particles may comprise a MMAD in the range of 0.5-5 um. In certain embodiments, one or more excipients is included in the suspending step. In various embodiments, the excipient may be a water soluble excipient, such as leucine, dileucine, trileucine, trehalose, mannitol, citrate, or acetate. In other embodiment, the excipient may be a water insoluble excipient, such as lecithin, DSPC or limonene. Such insoluble excipients may be dissolved in a non-aqueous medium that is miscible or immiscible with water, thereby creating an emulsion. Alternatively, a liposomal dispersion could be created into which the suspended imatinib could be added and homogenized or where it could be spray dried in separate feedstocks. These approaches are further described below.

The inhalable formulation may contain a therapeutically effective amount of imatinib particles for treating a condition of the pulmonary cardiovascular system. The condition of the pulmonary cardiovascular system can be pulmonary arterial hypertension (PAH).

In some embodiments, the inhalable formulation may comprise less than about 3% amorphous imatinib particles by mass. The inhalable formulation can comprise less than about 1% amorphous imatinib particles. The inhalable formulation may include less than 5% water or, in certain embodiments, less than 1% water by mass. In certain aspects, the invention may include an inhalable formulation produced by the above methods.

Aspects of the invention can include an inhalable formulation comprising micronized particles of imatinib, wherein the imatinib retains its crystal structure in the particles and the inhalable formulation comprises less than 5% amorphous imatinib particles by mass. The particles can comprise a size of about 0.5 to about 5 μm mass median aerodynamic diameter (MMAD). The inhalable formulation may further comprise one or more carrier agents.

In certain embodiments, the one or more carrier agents include lactose. Imatinib may be present in a therapeutically effective amount to treat a condition of the pulmonary cardiovascular system. The condition of the pulmonary cardiovascular system can be pulmonary arterial hypertension (PAH). In various embodiments, the inhalable formulation can comprise less than 3% amorphous imatinib particles. The inhalable formulation may comprise less than 1% amorphous imatinib particles. The inhalable formulation can include less than 5% water. In some embodiments, the inhalable formulation may comprise less than 1% water.

In certain aspects, the invention can include methods of treating a condition of the pulmonary cardiovascular system including providing to a subject an inhalable formulation comprising micronized particles of imatinib, wherein the imatinib retains its crystal structure in the particles and the inhalable formulation comprises less than 5% amorphous imatinib particles. In some embodiments, the subject may be a human.

BRIEF DESCRIPTION OF THE DRAWINGS

FIG. 3 diagrams steps of an exemplary method of preparing an inhalable formulation of imatinib.

DETAILED DESCRIPTION

Figure 1:
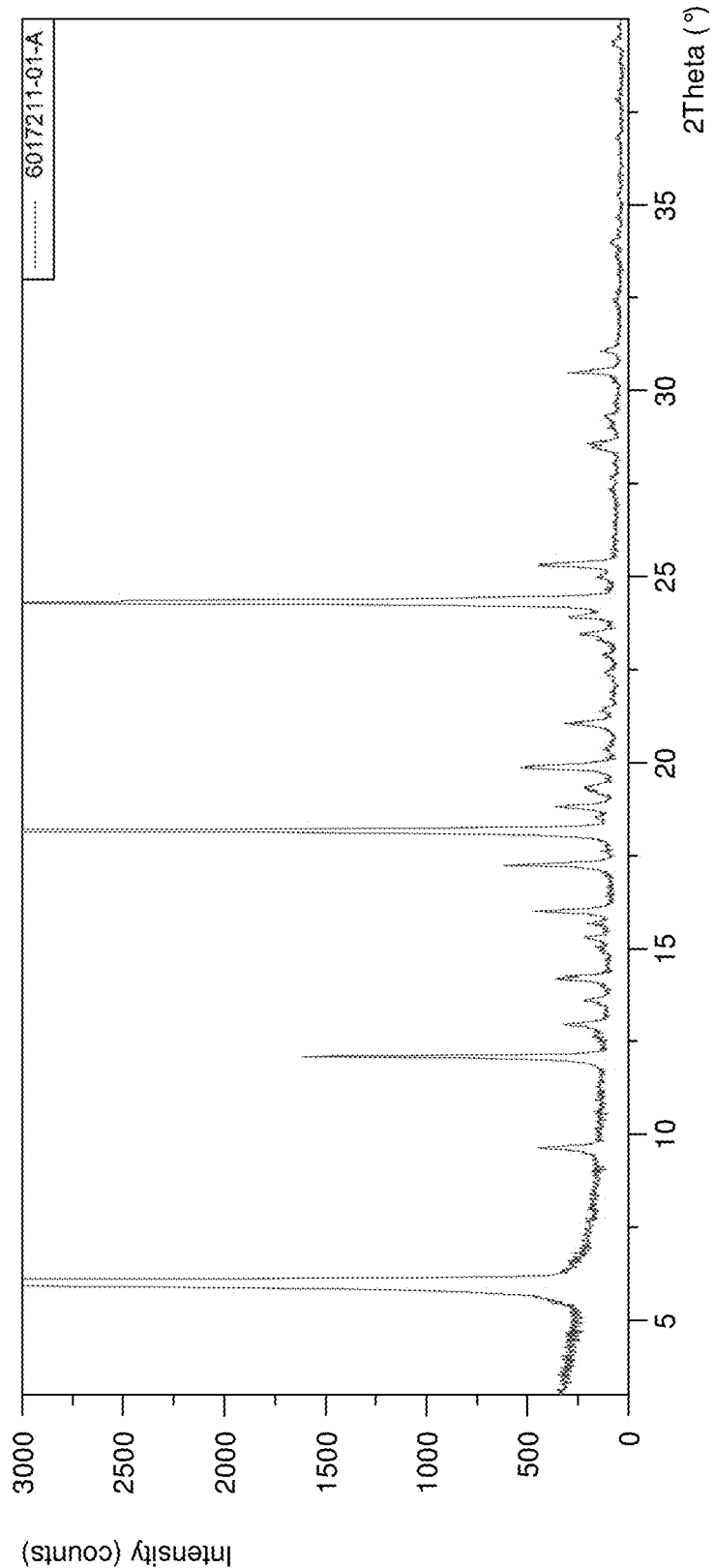
FIG. 1 shows an x-ray powder diffraction diagram of the type A crystal form of imatinib.

The invention relates to inhalable formulations of imatinib and salts thereof. Imatinib, as used throughout the application, refers to the free base compound unless a salt thereof is recited.

Imatinib as the free base has the below structure.

As used herein, imatinib is differentiated from imatinib mesylate (GLEEVEC).

The methods and compositions described herein provide greater concentrations of imatinib in target lung tissue than obtained with equivalent doses administered orally or through IV. Accordingly, methods and compositions of the invention allow for treatment of conditions of the pulmonary cardiovascular system (e.g., PAH) with lower doses than would be required in systemic administration, thereby lowering the risk of adverse events including subdural hematoma (See, Frost et al.). Thus, the invention provides viable treatment methods for life threatening disease that were heretofore too risky for practical application.

In certain embodiments, compounds of the invention include formulations of imatinib or salts thereof. In preferred embodiments, the free base imatinib is used in a formulation (either in dry powder or suspension) for inhalation to treat a condition of the pulmonary cardiovascular system such as PAH. While free base imatinib is preferred due to its desirable characteristics relative to imatinib mesylate (GLEEVEC) when used in inhalable formulations, certain salt forms are also contemplated. In various embodiments, imatinib salts that were found to exhibit suitable thermal stability and few or single polymorphic forms include glycollate, isethionate, malonate, tartrate, and malate. Other salt forms contemplated herein are xinafoate, furoate, trifenatate, HCl, sulfate, phosphate, lactate, maleate, fumarate, succinate, adipate, and citrate In various embodiments, micronized imatinib and salts thereof retain crystallinity, even after micronization and spray drying (as discussed in detail below). For example, imatinib formulations of the invention can include less than 50%, less than 25%, less than 20%, less than 10%, less than 9%, less than 8%, less than 7%, less than 6%, less than 5%, less than 4%, less than 3%, less than 2%, or less than 1% amorphous imatinib by mass. In preferred embodiments, formulations of the invention include no observable amorphous imatinib content. Of particular note is, by suspending micronized imatinib particles in a solution as opposed to solubilizing, the desired crystalline form and low amorphous content obtained during micronization is carried through to the spray-dried inhalable powder because the imatinib crystals are not dissolved in the solution to a significant degree.

Another unexpected result obtained with methods and formulations of the invention is that imatinib formulations of the invention are significantly less hygroscopic than conventional imatinib mesylate compounds. Accordingly, the imatinib formulations of the invention are better suited for dry powder inhalation and can comprise less than 5% water content, less than 4%, less than 3%, less than 2%, or, in preferred embodiments, less than 1% water content.

As discussed above, in order to accurately and consistently model pharmacokinetics of the imatinib formulations for proper dosing, low polymorphism is desired. To that end, inhalable formulations of the invention include imatinib or a salt thereof present in a single crystal form. In various embodiments, imatinib or a salt thereof may be present at greater than 75%, 80%, 85%, 90%, 95%, or, in preferred embodiments, greater than 99% in a single crystal form by mass. The single crystal form may be, for example, type A or type B in various embodiments.

Figure 2:
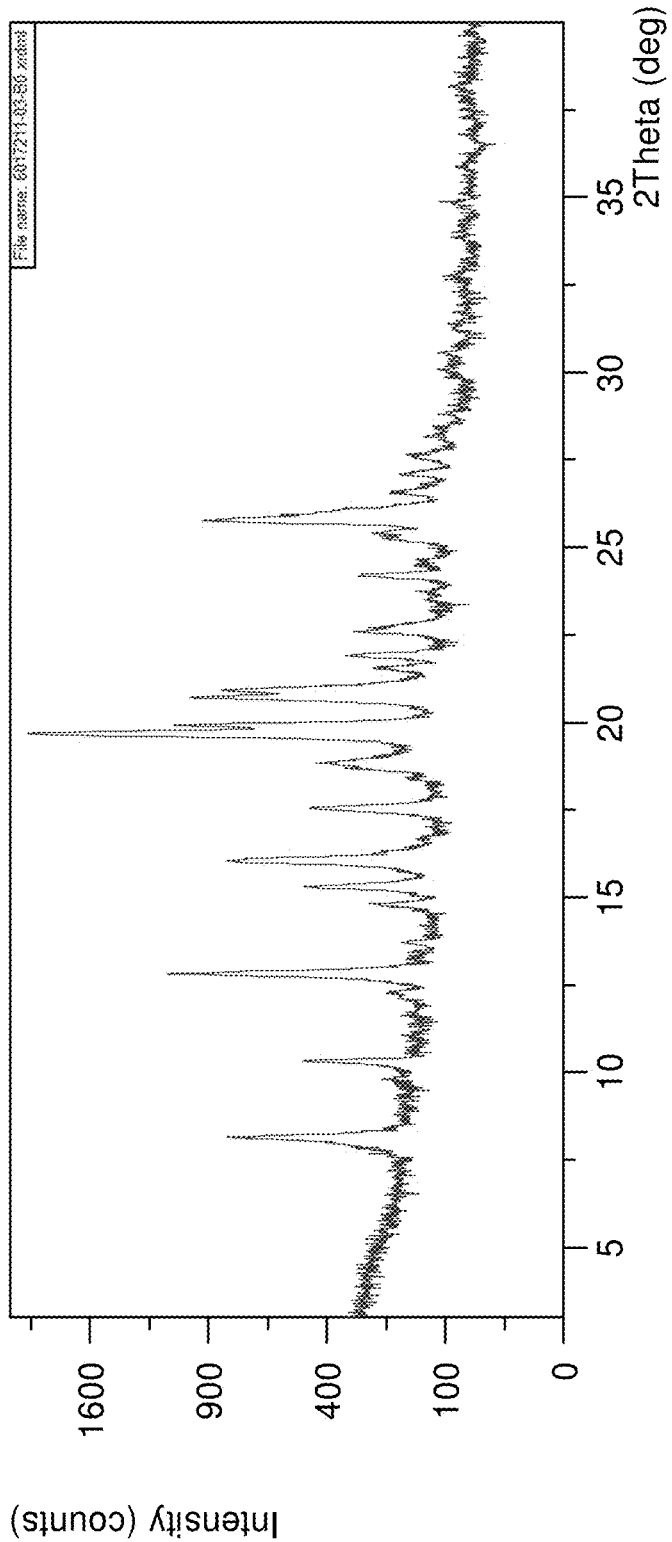
FIG. 2 shows an x-ray powder diffraction diagram of the type B crystal form of imatinib.

Crystalline purity can be estimated using any known method including, for example, x-ray powder diffraction (XRPD). An XRPD diagram for the type A crystal form of free base imatinib is shown in FIG. 1. An XRPD diagram for the type B crystal form of free base imatinib is shown in FIG. 2.

In various embodiments, imatinib or salts thereof are provided in dry powder formulations for inhalation. Dry powder can be administered via, for example, dry powder inhalers such as described in Berkenfeld, et al., 2015, Devices for Dry Powder Drug Delivery to the Lung, AAPS PharmaSciTech, 16(3):479-490, incorporated herein by reference. Dry powder compounds may be divided into single doses for single, twice daily, three times daily, or four times daily inhalation to treat disorders such as PAH or other conditions of the pulmonary cardiovascular system. The single doses may be divided into individual capsules or other formats compatible with the dry powder inhaler to be used.

In other embodiments, imatinib suspensions having the characteristics described herein (e.g., low polymorphism and amorphous content) can be delivered via inhalation using, for example, a nebulizer. Imatinib suspensions may offer advantages over solutions as discussed below. For nebulized suspensions, micronization and particle diameter may be of particular importance for efficient delivery and imatinib may be preferably micronized to a mass median diameter of 2 µm or less. The suspension solution for nebulizer inhalation can be aqueous and doses may be divided into individual containers or compartments for sterile storage prior to use.

Micronized imatinib particle size can range from about 0.5 µm to about 5 µm depending on application (e.g., dry powder or suspension for inhalation). In preferred embodiments the size range is about 1 µm to about 3 µm in dry powder formulations to achieve deep lung penetration. In certain embodiments, imatinib formulations of the invention may include one or more excipients. Excipients may include, for example, lactose in various forms (e.g., roller dried or spray dried). Larger lactose particles can be used as a carrier for inhalation of micronized imatinib formulations. The carrier particles, with their larger size, can be used to increase aerodynamic forces on the combined imatinib/carrier in order to aid in delivery through inhalation. Solvents may be used to condition the lactose surface such that the active component can be effectively separated from the lactose as it leaves the inhaler device and within the oral cavity when being used as a carrier. Magnesium stearate can be used as a force-control agent or conditioning agent in various embodiments. In some embodiments, leucine can be used as a force-control agent including different forms of leucine (e.g. isoleucine) along with dileucine and even trileucine.

Lecithin phospholipids such as DSPC may be used as an excipient for dry powder inhalation. In certain embodiments, excipients may include various hydrophilic polymers. See, for example, Karolewicz, B., 2016, A review of polymers as multifunctional excipients in drug dosage form technology, Saudi Pharm J., 24(5):525-536, incorporated herein by reference.

In various embodiments, the imatinib formulations of the invention may be pharmaceutical compositions for use in treating various conditions of the pulmonary cardiovascular system, such as PAH. For example, imatinib is a potent inhibitor of the platelet-derived growth factor receptor (PDGFR). Accordingly, the compositions of the invention may be used to treat any disease or disorder that involves inhibition of PDGFR or other kinases sensitive to imatinib.

In certain embodiments, the compositions of the invention may be used to treat PAH. For treatment of PAH or other disorders, a therapeutically effective amount of a pharmaceutical composition of imatinib according to the various embodiments described herein can be delivered, via inhalation (e.g., via dry powder inhaler or nebulizer) to deliver the desired amount of imatinib compound to the target lung tissue.

Dosages for treating PAH and other conditions of the pulmonary cardiovascular system may be in the range of between about 10 mg to about 100 mg per dose for inhalation on once, twice or three times per day schedule. About 0.1 mg to about 20 mg of the active imatinib compound may then be present at the lung after inhalation. In certain embodiments about 10 mg to 30 mg of imatinib may be given in a capsule for a single dry-powder inhalation dose with about 5 mg to about 10 mg of the compound may be expected to reach the lungs. In inhalable suspension embodiments, imatinib may be present at about 0.3 to about 1 mg/kg in a dose and may be administered one to four times a day to obtain the desired therapeutic results.

In certain embodiments, imatinib formulations of the invention may be used to treat pulmonary hypertension as a result of schistosomiasis. See, for example, Li, et al., 2019, The ABL kinase inhibitor imatinib causes phenotypic changes and lethality in adult Schistosoma japonicum, Parasitol Res., 118(3):881-890; Graham, et al., 2010, Schistosomiasis-associated pulmonary hypertension: pulmonary vascular disease: the global perspective, Chest, 137(6 Suppl): 20S-29S, the content of each of which is incorporated herein by reference.

Imatinib pharmaceutical compositions of the invention may be used to treat lung transplant recipients to prevent organ rejection. See, Keil, et al., 2019, Synergism of imatinib, vatalanib and everolimus in the prevention of chronic lung allograft rejection after lung transplantation (LTx) in rats, Histol Histopathol, 1:18088, incorporated herein by reference.

In certain embodiments, pharmaceutical compositions described herein can be used to treat pulmonary veno-occlusive disease (PVOD). See Sato, et al., 2019, Beneficial Effects of Imatinib in a Patient with Suspected Pulmonary Veno-Occlusive Disease, Tohoku J Exp Med. 2019 February; 247(2):69-73, incorporated herein by reference.

For treatment of any conditions of the pulmonary cardiovascular system for which imatinib may produce a therapeutic effect, compounds and methods of the invention may be used to provide greater concentration at the target lung tissue through inhalation along with consistent, predictable pharmacokinetics afforded by low polymorphism and amorphous content. The efficient localization of therapeutic compound at the target tissue allows for lower systemic exposure and avoidance of the adverse events associated with prolonged oral administration of imatinib mesylate.

Methods of the invention can include preparation of imatinib formulations. As noted above, imatinib or salts thereof may be administered via inhalation in suspension or dry powder form. Dry powder formulations may be obtained via any known method including, in preferred embodiments, jet milling. Jet milling can be used to grind imatinib and, potentially, various additives (e.g., excipients) using a jet (or jets) of compressed air or gas to force collisions between the particles as they transit at near sonic velocity around the perimeter of a toroidal chamber. The size reduction is the result of the high-velocity collisions between particles of the process material. Outputs of the jet mill may allow particles to exit the apparatus once a desired size has been reached. As noted herein, desired particle size for dry powder inhalation and other formulations may be in the range of about 0.5 µm to about 5 µm.

In certain embodiments, bulk imatinib may be micronized to the desired size for inhalation via wet milling wherein the imatinib particles are suspended in a slurry and reduced through shearing or impact with a grinding media.

An unexpected finding of the invention is that, once micronized, free base imatinib retains crystallinity and is considerably less hygroscopic than certain salt forms of imatinib (e.g., imatinib mesylate). Furthermore, micronized imatinib obtained using methods of the invention has been found to exhibit no apparent polymorphs other than the designated Type A and very low levels of amorphous content. Accordingly, this can result in improved stability of the drug substance and any drug product upon storage. Single crystal forms such as described may allow for more predictable in vivo behavior and appropriate dosing can be determined.

Once micronized, in dry powder form, imatinib formulations of the invention, with their low polymorphic and amorphous content, can be prepared for inhalation. In certain embodiments, the dry powder imatinib can be combined with larger carrier particles such as lactose as discussed above.

In some embodiments an imatinib suspension can be formed. The suspension may result from dry micronization followed by suspension of the resulting dry powder or can be obtained as the outcome of a wet milling procedure. Imatinib suspensions of micronized crystal forms may be used in nebulized inhalation treatment or may be spray dried for dry powder treatments.

FIG. 3 diagrams a spray drying method for preparing a dry powder imatinib formulation for inhalation. First, bulk imatinib is micronized 303 as described above to obtain imatinib particles in a desired size range. Then the micronized imatinib is suspended in a solution 305 such that they do not dissolve and instead retain the desired crystalline features (e.g., low polymorphism and amorphous content). The suspended particles can then be spray dried 307 using any known method. Spray drying techniques are well characterized and described, for example, in Ziaee, et al., 2019, Spray drying of pharmaceuticals and biopharmaceuticals: Critical parameters and experimental process optimization approaches, Eur. J. Pharm. Sci., 127:300-318, and Weers et al., 2019, AAPS PharmSciTech. 2019 Feb. 7; 20(3):103. doi: 10.1208/s12249-018-1280-0, and 2018/0303753, each of which is incorporated herein by reference. Spray drying micronized imatinib or salts thereof provides for uniform and predictable crystallinity and particle size and can avoid the need for large carrier molecules that may adversely affect the amount of inhaled drug that reaches the target lung tissue.

In spray-dried embodiments, micronized drug particles may be suspended within a non-aqueous solvent or within an emulsion of a non-aqueous solvent which, in turn is emulsified or dispersed within an aqueous environment (e.g. oil in water) and spray-dried, resulting in crystalline drug particles. The non-aqueous component may or may not be fugitive and thus could be removed completely during spray drying or, it could be retained, depending on the desired properties required. In such embodiments, each atomized droplet (mass median diameter ~10 μm) contains dispersed drug crystals. During the initial moments of the drying process, the more volatile aqueous phase begins to evaporate. The rapidly receding atomized droplet interface drives enrichment of the slowly diffusing drug and emulsion particles at the interface. This leads to formation of a void space in the center of the drying droplet. As the drying process continues, the less volatile oil phase in the emulsion droplets evaporates, resulting in formation of hollow pores in their place. Overall, the resulting hollow spray-dried composite particles contain drug crystals.

As maintaining a stable solution of crystalline imatinib is important to many features of the formulations and methods of the invention, formulation methods include manipulation of the suspension to prevent dissolution of the imatinib. Aqueous solution factors such as pH, ionic strength and dispersing agents may be used to obtain a stable suspension for nebulized inhalation or spray drying. For example, the pH of the aqueous solution may be adjusted to prevent dissolution. Solubility of the imatinib increases as the pH drops and, therefore, the pH of the aqueous solution in various embodiments may be above and, preferably, the solution may be neutral.

Additionally, the presence of ions in aqueous solution may tend to 'salt out' the imatinib. The solubility of the both imatinib and its mesylate salt may decrease with salinity. Accordingly, salt in the aqueous solution may be used to reduce solubility of the imatinib crystals in certain embodiments.

To promote dispersion and thoroughly deagglomerate the imatinib particles, a dispersing agent or surfactant (e.g., Tween 20 or Tween 80) may be added but should not cause dissolution of the imatinib in suspension.

In certain embodiments, excipients can be added to the suspension before spray drying. In various embodiments, the excipient may be a water-soluble excipient, such as leucine, dileucine, trileucine, trehalose, mannitol, citrate or acetate. In other embodiment, the excipient may be a water insoluble excipient, such as lecithin, distearylphosphatidylcholine (DSPC) or limonene. Such insoluble excipients may be dissolved in a non-aqueous medium that is miscible or immiscible with water, thereby creating an emulsion. Alternatively, a liposomal dispersion could be created into which the suspended imatinib could be added and homogenized or where it could be spray dried in separate feedstocks.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient, i.e., at least one a therapeutic compound of the invention and/or derivative thereof, in combination with a pharmaceutically acceptable carrier.

The effective dosage of each agent can readily be determined by the skilled person, having regard to typical factors each as the age, weight, sex and clinical history of the patient. In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the compounds of the present invention, or functional derivatives thereof. An "effective amount" is the amount as defined herein in the definition section and refers to an amount effective, at dosages and for periods of time necessary, to achieve the desired therapeutic result, e.g., a diminishment or prevention of effects associated with PAH. A therapeutically effective amount of a compound of the present invention or functional derivatives thereof may vary according to factors such as the disease state, age, sex, and weight of the subject, and the ability of the therapeutic compound to elicit a desired response in the subject. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to, or at an earlier stage of disease, the prophylactically effective amount may be less than the therapeutically effective amount. A prophylactically or therapeutically effective amount is also one in which any toxic or detrimental effects of the compound are outweighed by the beneficial effects.

Dosage regimens may be adjusted to provide the optimum desired response (e.g. a therapeutic or prophylactic response). For example, a single inhalable bolus may be administered, several divided doses may be administered over time or the dose may be proportionally reduced or increased as indicated by the exigency of the therapeutic situation. Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the patient.

The term "dosage unit" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound, and (b) the limitations inherent in the art of compounding such an active compound for the treatment of sensitivity in individuals.

In some embodiments, therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is sufficient to reduce PAH symptoms in a subject. In some embodiments, the therapeutically effective amount is sufficient to eliminate PAH symptoms in a subject.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability, or half-life of the compounds of the invention or functional derivatives thereof, and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more compounds of the invention or functional derivatives thereof are optionally tested in one or more appropriate in vitro and/or in vivo animal models of disease, such as models of PAH, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of compounds of the invention or functional derivatives thereof at various concentrations, e.g., as applied to the mass and overall health of the patient. Administration can be accomplished via single or divided doses.

In certain embodiments, in which an aqueous suspension is part of the manufacturing process, the aqueous suspension may contain the active material in admixture with excipients suitable for the manufacture of aqueous suspensions. Such excipients are suspending agents dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, mannitol, or trehalose.

Dispersible powders and granules suitable for preparation of an aqueous suspension by the addition of water provide the active ingredient in admixture with a dispersing or wetting agent, suspending agent and one or more preservatives.

The term "pharmaceutical composition" means a composition comprising a compound as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. The term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response, and the like, and are commensurate with a reasonable benefit/risk ratio.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Intratracheal instillation of imatinib in an animal model was found to provide significantly (e.g., 25 times higher as measured via AUC) lung exposure to the compound compared to oral or IV administration. Accordingly, lower doses of imatinib can be provided through inhalation while still providing the same or greater concentration in the target lungs thereby achieving the desired therapeutic effects with diminished risk of adverse events. TABLE 1 shows lung level comparisons in an animal model of various doses of imatinib and imatinib mesylate suspensions and solutions administered orally or via intratracheal instillation (IT) or intravenous (IV).

TABLE 1

Figure 4:
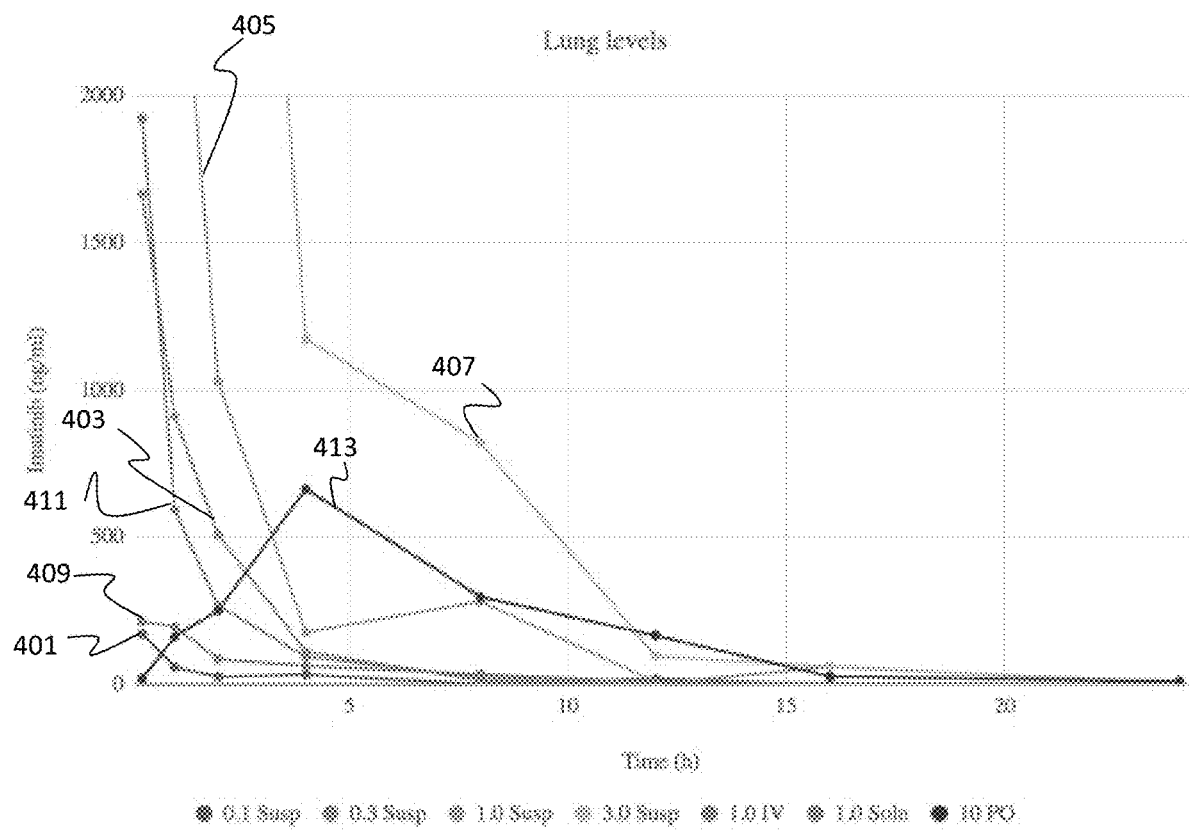
FIG. 4 shows imatinib lung levels over time for various doses of imatinib solutions and suspensions delivered via various administration routes.

| Route | Form | Dose (mg/kg) | AUC (h*ng/g) | Dose multiple vs. Oral | FIG. 4 Indicator |
|---|---|---|---|---|---|
| IT | suspension | 3 | 379659 | 27.4 | 407 |
| IT | suspension | 1 | 96981 | 21.0 | 405 |
| IT | suspension | 0.3 | 40986 | 29.6 | 403 |
| IT | suspension | 0.1 | 4707 | 10.2 | 401 |
| IT | solution-mesylate | 1 | 41852 | 9.1 | 411 |
| IV | solution-mesylate | 1 | 7794 | 1.7 | 409 |
| Oral | solution-mesylate | 10 | 46223 | 1 | 413 |

FIG. 4 shows lung concentrations of imatinib over time of the various forms and routes described in TABLE 1. The suspensions administered via IT were found to maintain levels above IC50 long enough to allow for TID or even BID dosing for inhaled solutions. The plotted routes, forms, and doses are indicated in TABLE 1 above.

Figure 5:
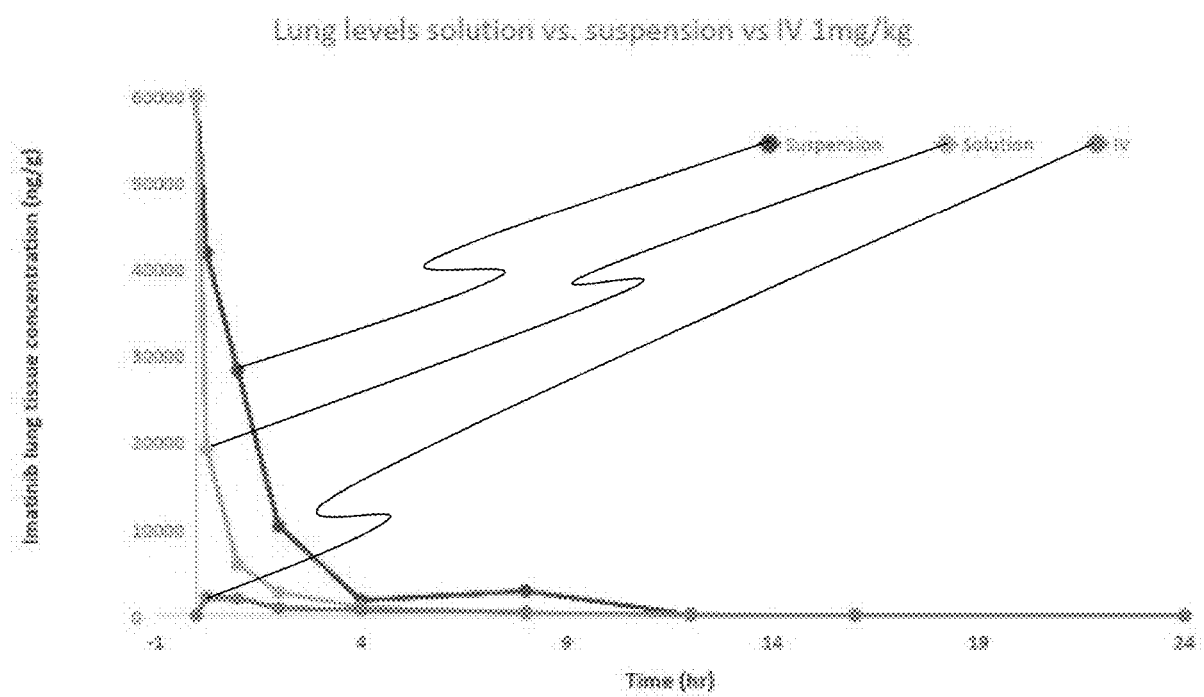
FIG. 5 shows an imatinib lung concentration comparison between 1 mg/kg of imatinib suspension or solution delivered by intratracheal instillation and 1 mg/kg of imatinib delivered by IV.

FIG. 5 shows lung concentrations of imatinib solution and suspensions administered via IT compared to lung concentrations of an IV solution of imatinib at 1 mg/kb dose and illustrates a clear AUC advantage in the IT suspension over the IT solution and both over the IV solution.

Example 2

Initial physicochemical characterization of unmicronized and micronized Imatinib Free Base was performed using an array of techniques. Imatinib free base was obtained as a dry powder.

Particle size reduction of Imatinib Free Base was performed using a 2-inch air jet mill (Food Pharma Systems, PM-2, Italy). The system was operated under nitrogen at a venturi and ring pressure of 8 bar and 7 bar, respectively. A total of 8.00 g of raw Imatinib Free Base material was micronized. The rate at which the material was introduced into the mill was approximately 0.5 g/min. All samples were collected and stored in an amber glass jar, which was then sealed in aluminium laminate pouch.

Figure 6:
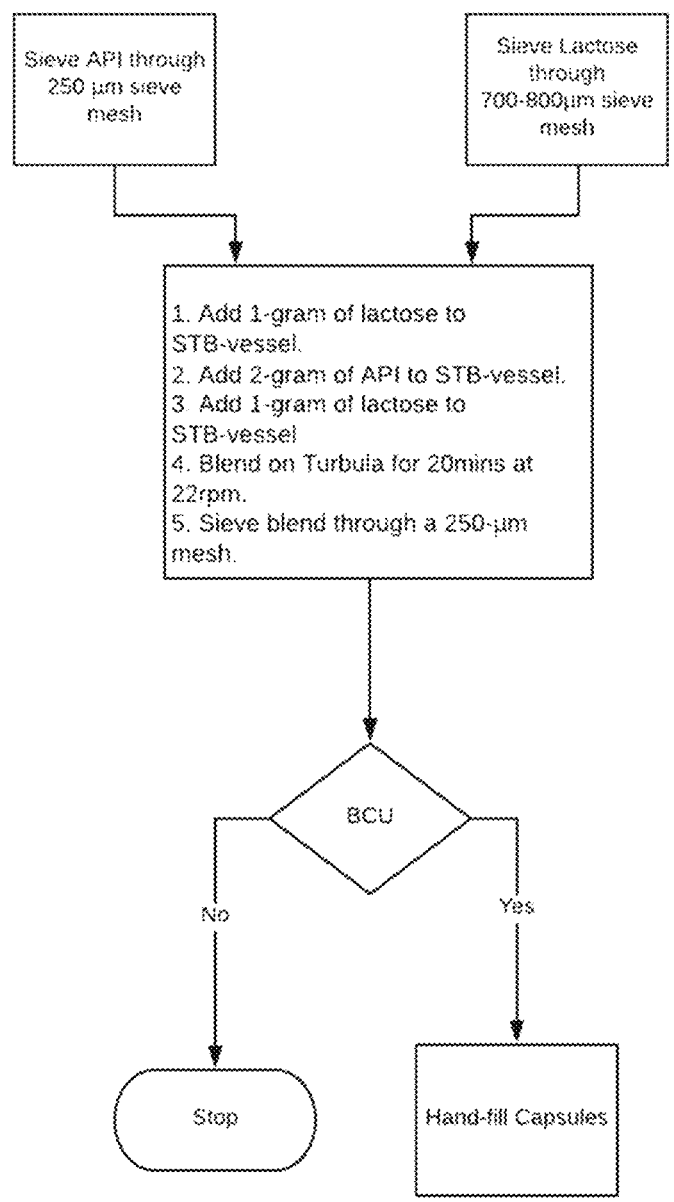
FIG. 6 diagrams exemplary processing steps for inhalable imatinib preparations.

Micronized material was used to manufacture a 50% drug load with inhalation grade lactose (Respitose ML001, available from DFE pharma, Germany). This formulation was manufactured at 4-gram total batch size using low shear blending. An STB-50 vessel was used for the manufacture. The processing steps are shown in the flow diagram in FIG. 6. This formulation equated to a 10 mg nominal dose per 20 mg of powder.

After conducting blend content uniformity (BCU) measurements, formulations (20.0±0.2 mg) was filled into size 3 Hydroxypropyl methylcellulose (HPMC) capsules by hand. Filled capsules were tested for emitted dose by a Dosage Unit Sampling Apparatus (DUSA) and total lung dose using an OPC-standard anatomical throat. The inhaler used for this component of the study was a HR-RS01 (Plastiape, Italy) at 60 L/min.

A feasibility batch was manufactured on small scale (2 g) using a Buchi B290 laboratory spray dryer (see Table 2 below). Micronized Imatinib was suspended in water at an API:Leucine ratio of 75:25 w/w. The aspiration rate was at the highest setting, maximum suitable atomisation pressure and feed rate of 2-4 mL/min. Spray drying conditions was checked by assessment of yield, powder appearance and PSD during the run.

TABLE 2

| | Spray drying formulation in water |
|---|---|
| Imatinib (micronized) | 1500 mg |
| Leucine | 500 mg |
| NaCl | N/A |
| Total solids | 2000 mg |
| Water | 25 mL (8% w/v solids) |
| % dissolved imatinib | 0.01% w/w (150 micrograms) |
| % imatinib in the soluble components | 0.03% w/w |

For particle sizing, unmicronized imatinib was dispersed with compressed air (2 bar) and sized by laser diffraction (RODOS dry powder feeder; HELOS laser diffractometer, WINDOX 4.0 software; Sympatec GmbH, Germany). The 10, 50 and 90% undersize particle size values (×10, ×50 and ×90, respectively) were obtained. To evaluate the extent of cohesion between particles, values of ×50 were measured (n=3) over the pressure range of 1-3 bar for the micronized material.

The specific surface area (SSA) of Imatinib samples (0.6 g) was measured using a Micrometrics TriStar 3000 surface area analyser (Micromeritics Instrument Corporation, Norcross, USA). An eleven-point BET nitrogen adsorption analysis was carried out in triplicate after degassing the samples for 16 hours in a FlowPrep 060 degasser at 25° C. (Micromeritics Instrument Corporation, Norcross, USA).

To determine the X-ray powder diffraction (XRPD) pattern of the FP samples, all samples were analyzed on a Bruker Powder Diffractometer (D8; Bruker AXS Inc., Madison, USA) using CuKα radiation ($\lambda$=1.54 Å). The data were collected over a single 2θ sweep with range 2θ=2–40°2θ and step time 0.2 s.

The thermal properties of all samples were investigated using a differential scanning calorimeter (DSC 8000, PerkinElmer, UK), calibrated with an indium standard. Approximately 3 mg of sample was accurately weighted into an aluminum pan and crimped with a lid to form a hermetic seal. The sample and reference pan were heated at a rate of 10° C./min from 20° C. to 300° C. The calorimeter head was continuously flushed with dry nitrogen gas at 0.2 L/min during all measurements. Thermalgravimetric analysis was performed with a PerkinElmer Pyris 1 using aluminum vented pans in ceramic crucibles. The samples were heated at a rate of 10° C./min from 20° C. to 400° C.

Figure 7:
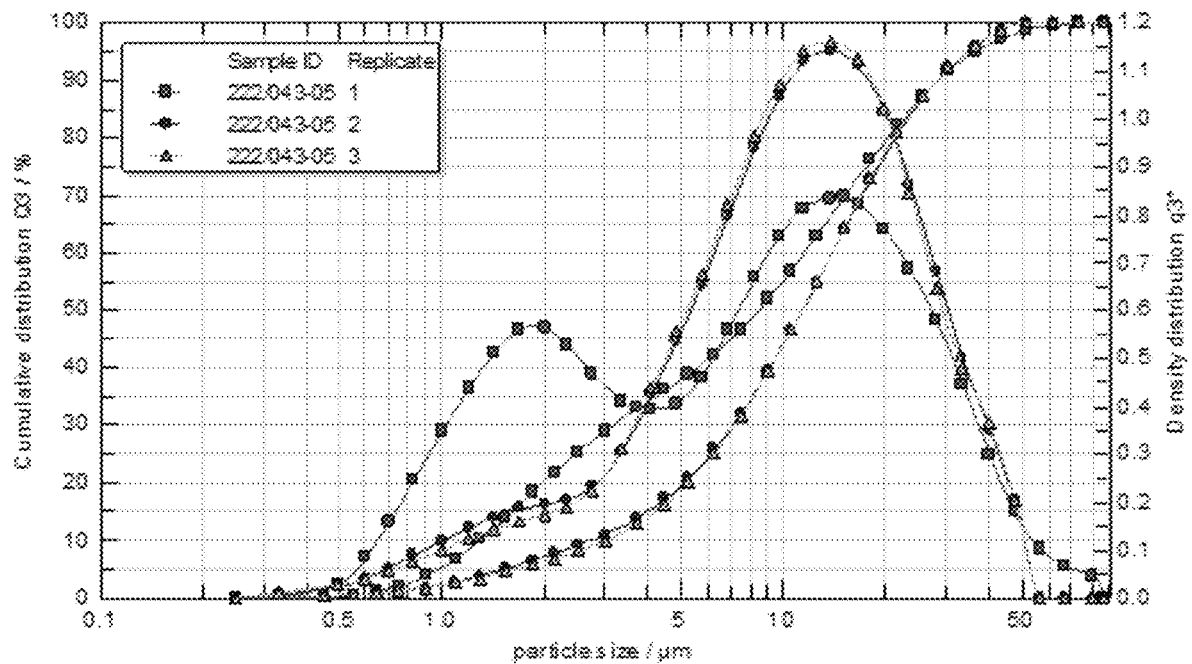
FIG. 7 shows particle size distribution (PSD) analysis of unmicronized imatinib.
Figure 8:
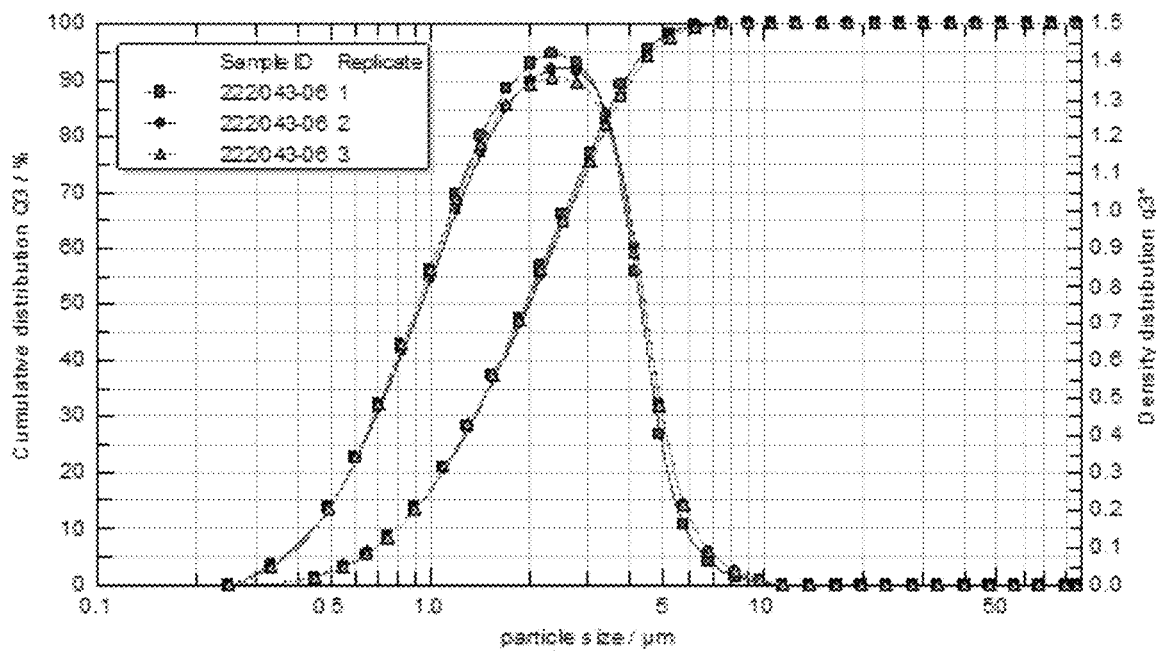
FIG. 8 shows PSD analysis of micronized imatinib at 1 bar.
Figure 9:
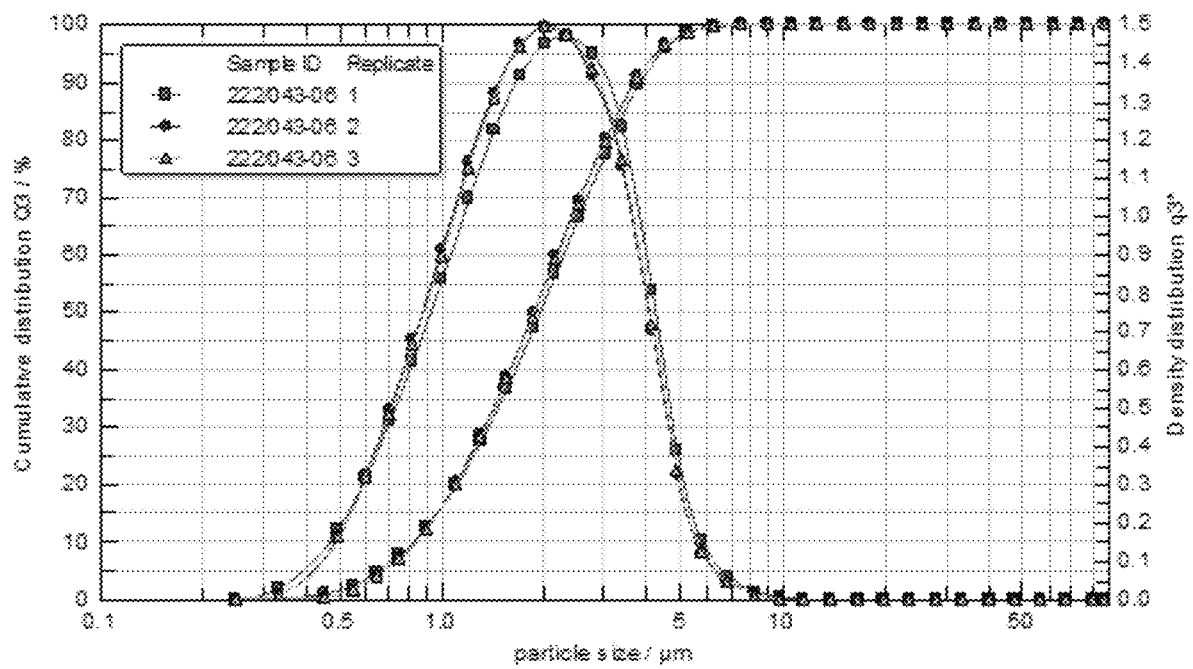
FIG. 9 shows PSD analysis of micronized imatinib at 2 bar.
Figure 10:
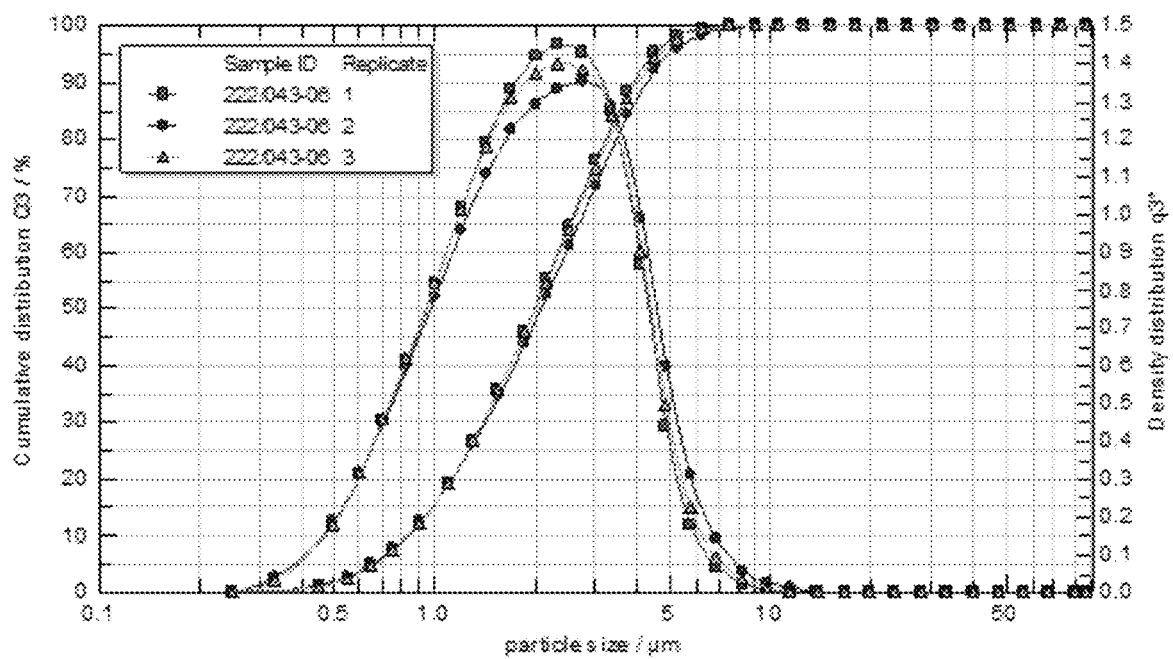
FIG. 10 shows PSD analysis of micronized imatinib at 3 bar.

Particle size distribution (PSD) analysis of the unmicronized material is shown in FIG. 7 and micronized material is shown at 1, 2, and 3 bar in FIGS. 8-10, respectively. These data are also summarized in Table 3. In addition, the specific surface area of unmicronized and micronized Imatinib freebase is shown in TABLE 4.

TABLE 3

Particle size distribution of unmicronized, micronized and co-spray dried Imatinib.

| Dispersing Conditions | $d_{10}$/μm (SDev) | $d_{50}$/μm (SDev) | $d_{90}$/μm (SDev) |
|---|---|---|---|
| Un-Micronized material | | | |
| 2 bar | 2.38 (0.94) | 10.42 (1.65) | 28.68 (0.24) |
| Micronized material | | | |
| 1 bar | 0.80 (0.00) | 1.95 (0.03) | 4.00 (0.10) |
| 2 bar | 0.83 (0.01) | 1.89 (0.05) | 3.74 (0.08) |
| 3 bar | 0.83 (0.00) | 2.01 (0.05) | 4.11 (0.18) |
| Spray Dried | | | |
| | 0.79 (0.01) | 3.02 (0.02) | 8.04 (0.10) |

TABLE 4

Specific surface area (SSA) analysed by BET of unmicronized and micronized Imatinib.

| Material | SSA (m2/g) | Mean SSA (m2/g) | Std. Dev. |
|---|---|---|---|
| Un-Micronized | 0.88 0.87 | 0.88 | 0.00 |
| Micronized | 7.29 | 7.85 | 0.80 |

Unmicronized Imatinib had a median particle size of 10.4 μm and 10% and 90%-undersize of 2.38 and 28.68 μm, respectively. The span of the PSD of the unmicronized material was 2.53. The surface area of the unmicronized material was 0.88 m2/g.

From the 8 g of unmicronized material that was air-jet micronized, a total of 5.6 g of micronized material was collected. This equated to a product yield of 71.3%. The surface area of the micronized material was 7.9 m2/g, suggesting that the micronization process was successful in creating new surface area and reduction of particle size. For the suspension spray-dried material with leucine, the yield from the process was approximately 80% and presented good flow properties.

The median particle size of the micronized material when dispersed at 1, 2 and 3 bar was 1.95, 1.89 and 2.01 μm, respectively. The 10%-undersize ranged from 0.80-0.83 μm and 90%-undersize ranged from 3.74-4.11 μm. These data suggest the new micronized Imatinib had a slightly finer particle size than the material micronized in report 20181026-106-001 v3.0. That material had d10, d50 and d90 of 1.25, 2.07 and 3.41 μm, respectively.

Figure 11:
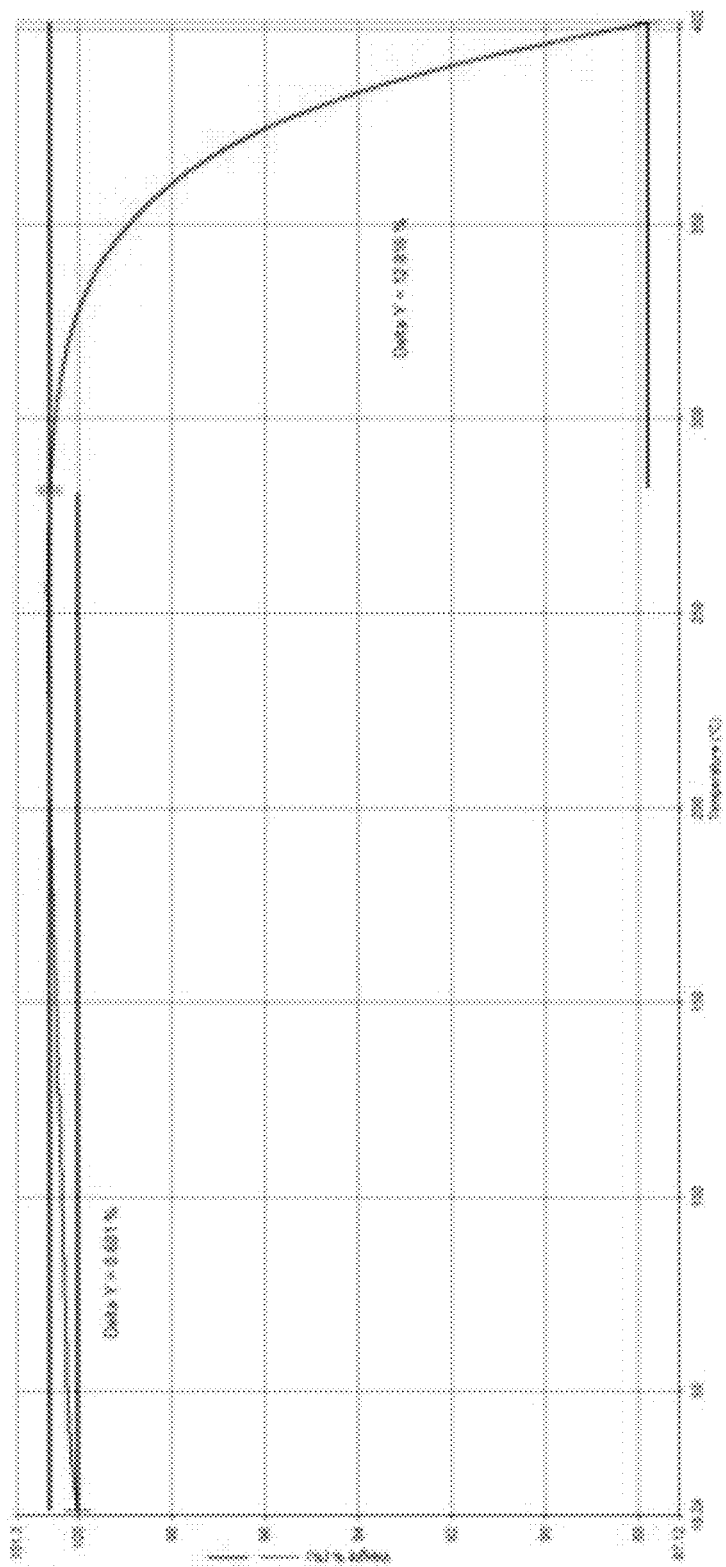
FIG. 11 shows thermalgravimetric analysis (TGA) of imatinib Free Base, pre-micronization.

The particle size in terms of d10, d50 and d90 was 0.79, 3.02 and 8.04 μm, respectively. These data suggested that the spray-drying of suspended micronized Imatinib had a modestly larger particle size. The un-micronized sample was analyzed by thermogravimetric analysis (TGA) to determine the decomposition temperature prior to differential scanning calorimeter (DSC) analysis. It was concluded that the sample starts to decompose at approx. 300° C. and therefore the DSC analysis was set for 20-300° C. (FIG. 11).

Figure 12:
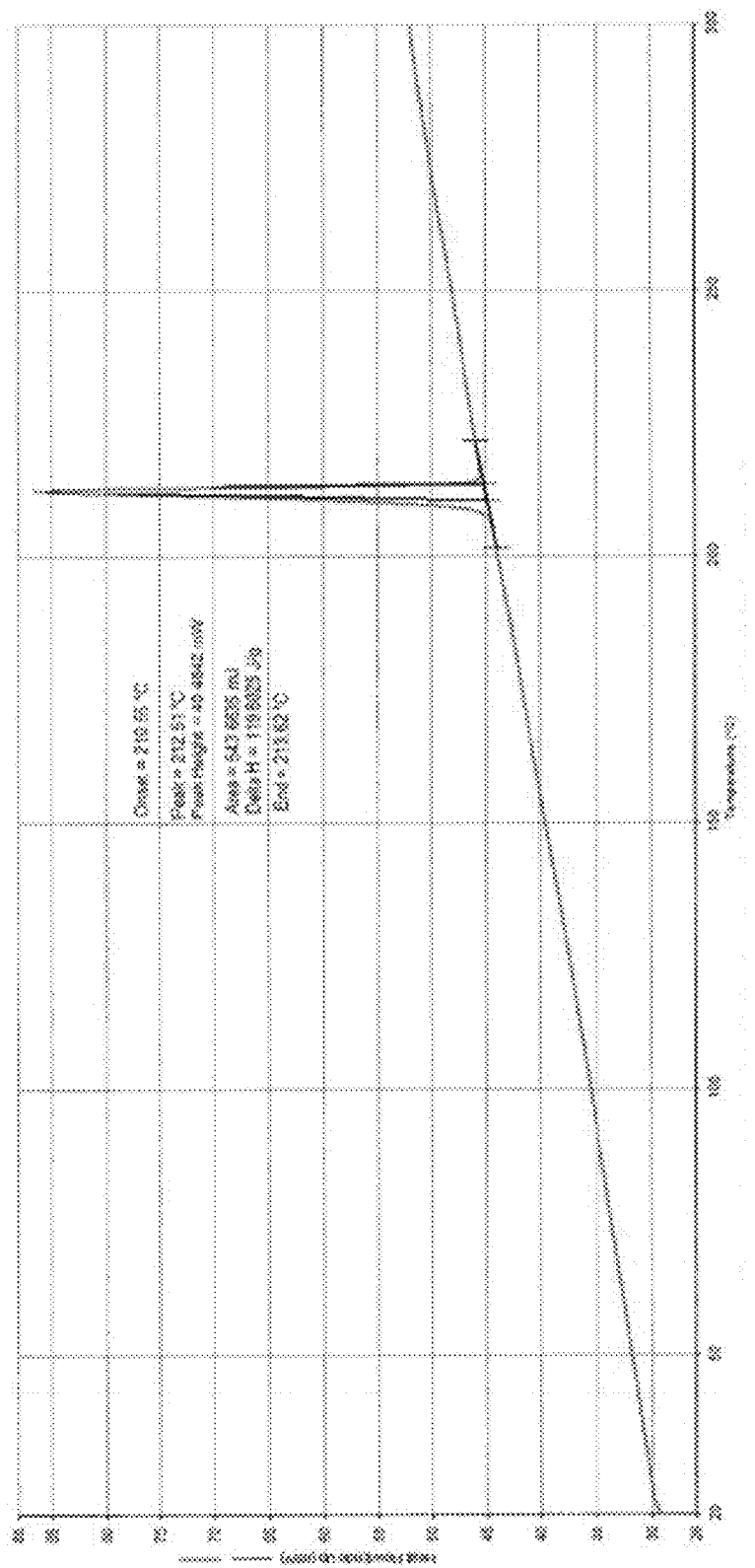
FIG. 12 shows a differential scanning calorimeter (DSC) thermogram of un-micronized imatinib.
Figure 13:
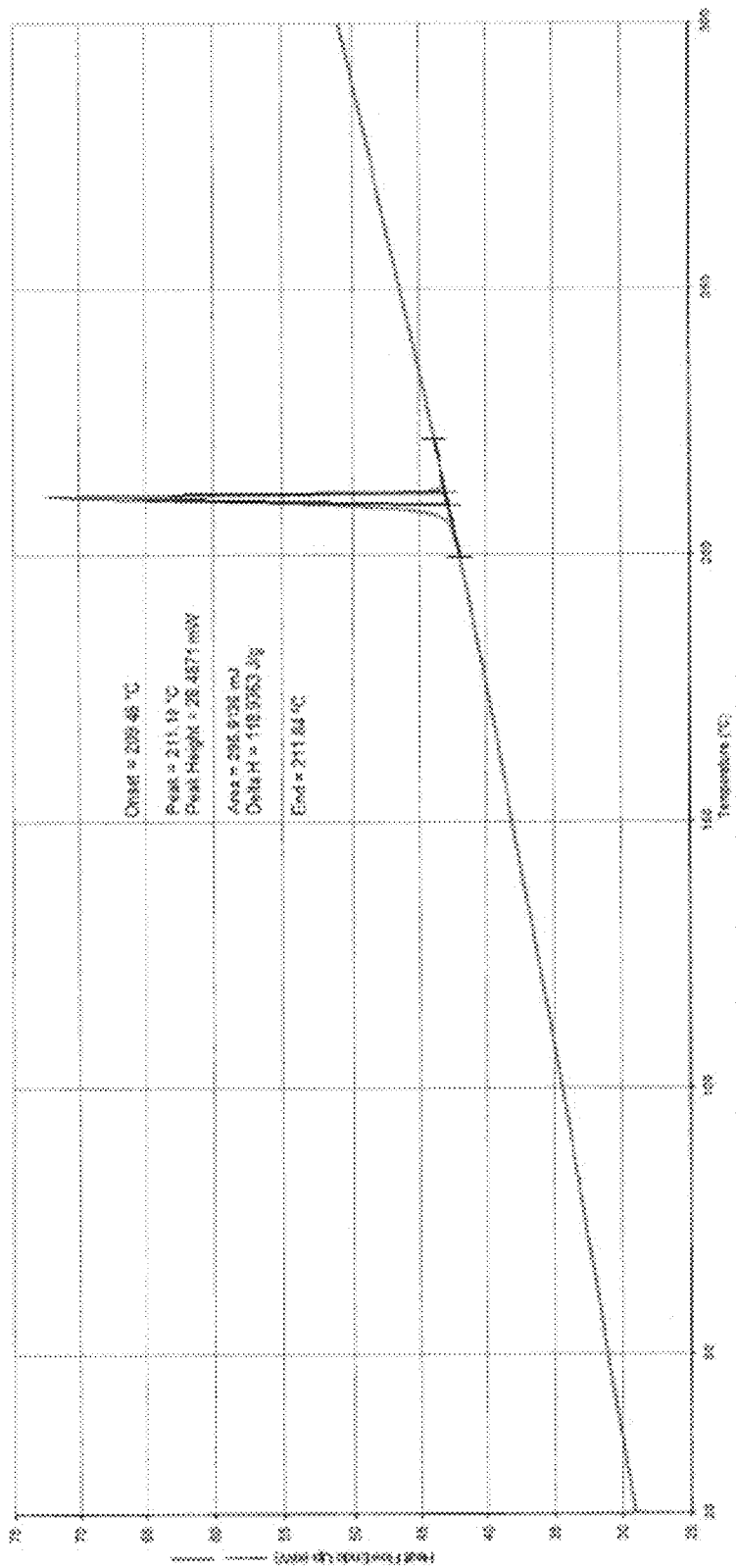
FIG. 13 shows a DSC thermogram of micronized imatinib.

The DSC thermograms of unmicronized and micronized imatinib are shown in FIGS. 12 and 13, respectively. DSC of the Free Base suggested a large endothermic event with an onset of ca. 210° C. (peak at ca. 212° C.), which was most likely associated with material melting. The imatinib exhibited similar DSC thermograms for both the un-micronized and micronized material with a melt onset of approx. 210° C. and peak enthalpies of approx. 119 J/g.

Figure 14:
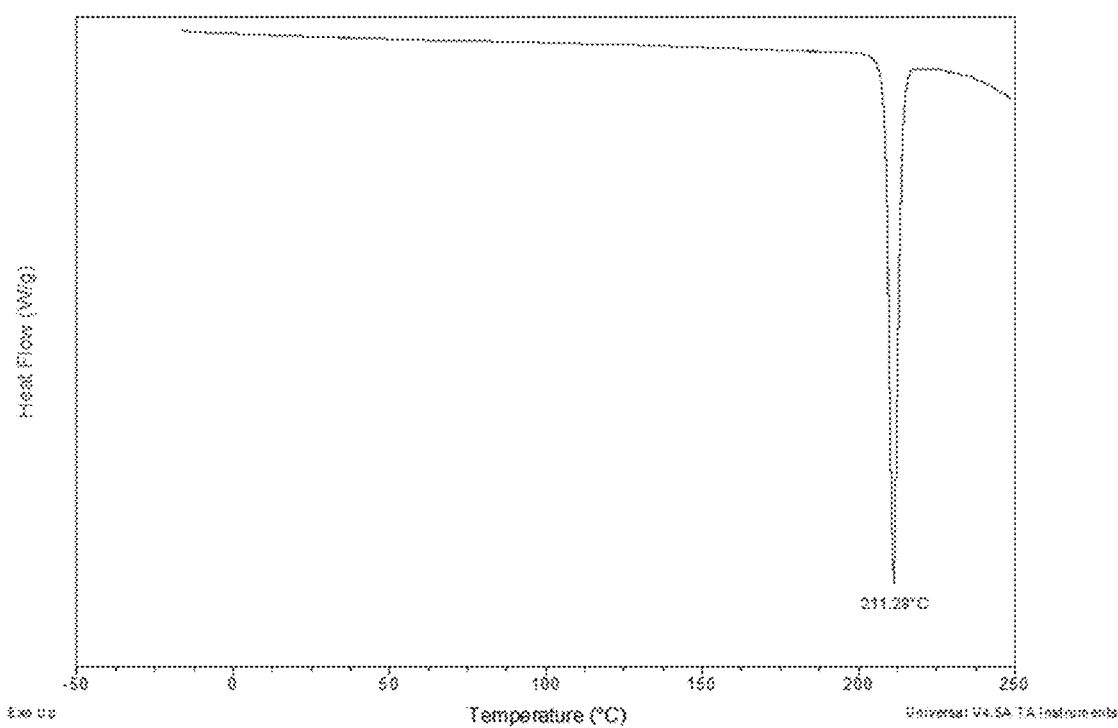
FIG. 14 shows a DSC thermogram of co-spray-dried imatinib with leucine.

The DSC trace of spray-dried Imatinib/leucine batch is shown in FIG. 14. The material shows a melting event at 211° C. associated with Imatinib melting. There was no cold crystallization or Tg. This suggests that the material remained completely crystalline.

The combination of lactose ML001 containing imatinib at 50% w/w was evaluated. This formulation was tested for the Total Lung Dose by Anatomical Throat (n=3), ED by DUSA with the High Resistance RS01 and PSD by Sympatec (0.5, 1 and 2 bar).

Figure 15:
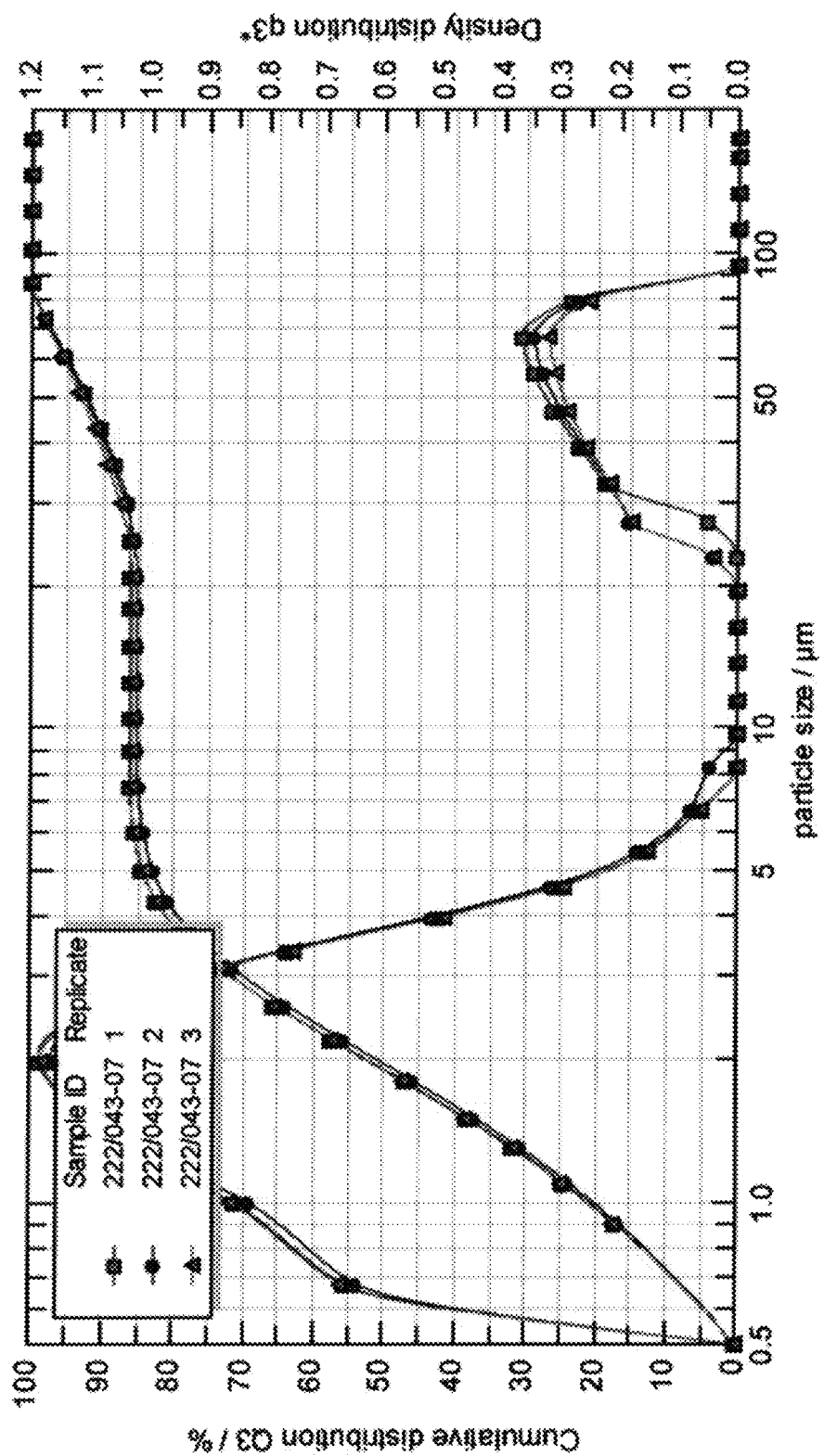
FIG. 15 shows PSD analysis of various carrier-based imatinib samples discussed in Example 2.

The capsule content uniformity and preliminary aerosolization data using a coated OPC anatomical throat are shown in Tables 5 and 6, respectively. In addition, the single actuation content is shown in Table 7. The particle sizing of the formulation is summarized in Table 8 and shown in FIG. 15.

TABLE 5

% Assay per 10 random capsules filled with carrier-based formulation.

| | Assay % |
|---|---|
| Sample 1 | 96.21 |
| Sample 2 | 98.27 |
| Sample 3 | 95.91 |
| Sample 4 | 94.21 |
| Sample 5 | 99.00 |
| Sample 6 | 96.51 |
| Sample 7 | 99.25 |
| Sample 8 | 98.17 |
| Sample 9 | 95.74 |
| Sample 10 | 96.24 |
| MEAN | 97.03 |
| STDEV | 1.713 |
| % RSD | 1.765 |
| USP <905> AV | 5.581 |

TABLE 6

| Emitted dose, deposition in anatomical throat and total lung dose post aerosolization from a high-resistance RS01 at 60 L/min. | | | | | |
|---|---|---|---|---|---|
| | 1 | 2 | 3 | Average/ mg | SD |
| Emitted Dose/mg | 6.65 | 7.16 | 6.13 | 6.64 | 0.51 |
| Anatomical Throat Deposition/mg | 1.97 | 2.41 | 1.83 | 2.07 | 0.30 |
| Total Lung Dose/mg | 4.60 | 4.62 | 4.22 | 4.48 | 0.22 |

TABLE 7

Emitted dose by DUSA performed using a high-resistance RS01 at 60 L/min.

| | Target DD % |
|---|---|
| Sample 1 | 69.04 |
| Sample 2 | 69.02 |
| Sample 3 | 67.95 |
| Sample 4 | 63.39 |
| Sample 5 | 65.95 |
| Sample 6 | 76.04 |
| Sample 7 | 72.84 |
| Sample 8 | 71.30 |
| Sample 9 | 70.24 |
| Sample 10 | 71.27 |
| MEAN | 69.7 |
| STDEV | 3.6 |
| % RSD | 5.14 |

TABLE 8

Particle size distribution of formulation NP-106-18104-001

| Dispersing Conditions | $d_{10}$/μm (SDev) | $d_{50}$/μm (SDev) | $d_{90}$/μm (SDev) | VMD (μm) |
|---|---|---|---|---|
| | Formulation 50% w/w drug load | | | |
| 2 bar/15 mm/s | 0.74 | 1.92 | 42.89 | 9.36 |
| | 0.74 | 1.97 | 41.40 | 9.45 |
| | 0.73 | 1.91 | 39.12 | 8.98 |
| Average | 0.74 | 1.93 | 41.14 | 9.26 |
| Std. Dev. | 0.01 | 0.03 | 1.90 | 0.25 |
| % RSD | 0.78 | 1.66 | 4.62 | 2.69 |

The emitted dose from the device was 6.6 mg and total lung dose was approximately 4.5 mg. These data suggest a high-payload of active was able to achieve high lung delivery. Single actuation content ranged from 63-71% delivered normalized to the nominal loaded dose. These data suggested good delivery efficiency of the formulation. Particle sizing of the formulation suggested a bimodal distribution. The volume weighted median diameter was 9.3 μm and the 90% undersize was 41 μm and is related to the coarser carrier in the formulation. These data suggest that the high-payload carrier formulation exhibited good aerosolization efficiency.

The combination of 25% w/w leucine and 75% w/w imatinib was also evaluated. This formulation was tested for the Total Lung Dose by Anatomical Throat (n=3), ED by DUSA with the High Resistance RS01. Target fill weight of the formulation in the capsule was 15.00±0.75 mg.

The capsule content uniformity and preliminary aerosolization data using a coated OPC anatomical throat are shown in Tables 9 and 10, respectively. These data suggested good capsule content uniformity.

The emitted dose from the device of the spray dried formulation was 8.3 mg and total lung dose was approximately 6.9 mg. The throat deposition was lower than the high payload carrier formulation and the delivery efficiency was better than the carrier-based formulation. Single actuation content ranged from 72-85% delivered normalized to the nominal loaded dose. These data suggested good delivery efficiency of the spray-dried formulation, which had higher lung dose, higher emitted dose and lower throat deposition than the high-payload carrier formulation. Table 11 shows the emitted dose data.

TABLE 9

% Assay per 10 through life capsules filled with carrier-based formulation.

| | Assay % |
|---|---|
| Sample 1 | 104.61 |
| Sample 2 | 111.97 |
| Sample 3 | 103.92 |
| Sample 4 | 99.11 |
| Sample 5 | 109.32 |
| Sample 6 | 101.90 |
| Sample 7 | 107.81 |
| Sample 8 | 103.81 |
| Sample 9 | 88.23 |
| Sample 10 | 106.49 |
| MEAN | 103.72 |
| STDEV | 6.575 |
| % RSD | 6.340 |
| USP <905> AV | 17.99 |

TABLE 10

| Emitted dose, deposition in anatomical throat and total lung dose post aerosolization from a high-resistance RS01 at 60 L/min. | | | | | |
|---|---|---|---|---|---|
| | 1 | 2 | 3 | Average/ mg | SD |
| Emitted Dose/mg | 8.24 | 8.10 | 8.67 | 8.34 | 0.32 |
| Anatomical Throat Deposition/mg | 1.34 | 1.33 | 1.33 | 1.33 | 4.62 |
| Total Lung Dose/mg | 6.81 | 6.67 | 7.25 | 6.91 | 0.30 |

TABLE 11

Emitted dose by DUSA performed using a high-resistance RS01 at 60 L/min.

| | Target DD % |
|---|---|
| Sample 1 | 79.94 |
| Sample 2 | 86.02 |
| Sample 3 | 73.42 |
| Sample 4 | 72.14 |
| Sample 5 | 81.87 |
| Sample 6 | 75.82 |
| Sample 7 | 74.05 |
| Sample 8 | 85.60 |
| Sample 9 | 80.04 |
| Sample 10 | 85.50 |
| MEAN | 79.4 |
| STDEV | 5.3 |
| % RSD | 6.72 |

What is claimed is:

1. A method of preparing an inhalable formulation comprising:

micronizing imatinib freebase particles having type A crystal structure, the micronized imatinib freebase particles having a mass median aerodynamic diameter in the range of about 0.5 µm to about 5 µm;

suspending the micronized imatinib freebase particles in a solution;

spray drying the suspended micronized imatinib freebase particles to prepare an inhalable formulation thereof comprising less than 5% amorphous imatinib freebase particles and less than 5% water, wherein imatinib freebase is the only active pharmaceutical ingredient in the inhalable formulation.

2. The method of claim 1 wherein one or more excipients is included in the suspending step.

3. The method of claim 2 wherein the excipient is a water soluble excipient selected from the group consisting of leucine, dileucine, trileucine, trehalose, mannitol, citrate, and acetate.

4. The method of claim 2 wherein the excipient is a water insoluble excipient selected from the group consisting of lecithin and distearylphosphatidylcholine (DSPC).

5. The method of claim 1 wherein the inhalable formulation contains a therapeutically effective amount of imatinib freebase for treating a condition of the pulmonary cardiovascular system.

6. The method of claim 5 wherein the condition of the pulmonary cardiovascular system is pulmonary arterial hypertension (PAH).

7. The method of claim 1 wherein the inhalable formulation comprises less than 1% amorphous imatinib freebase particles.

8. The method of claim 1 wherein the inhalable formulation comprises less than 1% water.

* * * * *